United States Patent [19]

Bach, Jr.

[11] Patent Number: 4,850,357

[45] Date of Patent: Jul. 25, 1989

[54] BIPHASIC PULSE GENERATOR FOR AN IMPLANTABLE DEFIBRILLATOR

[75] Inventor: Stanley M. Bach, Jr., Shoreview, Minn.

[73] Assignee: Cardiac Pacemakers, Inc., St. Paul, Minn.

[21] Appl. No.: 143,061

[22] Filed: Jan. 12, 1988

[51] Int. Cl.$^4$ .............................................. A61N 1/00
[52] U.S. Cl. ................................................ 128/419 D
[58] Field of Search ............ 128/419 D, 419 PG, 421, 128/696; 307/106

[56] References Cited

U.S. PATENT DOCUMENTS

| | | | |
|---|---|---|---|
| 3,206,313 | 12/1972 | Milani et al. | 128/419 D |
| 3,241,555 | 3/1966 | Caywood et al. | 128/419 D |
| 3,359,984 | 12/1967 | Daniher | 128/419 D |
| 4,440,172 | 4/1984 | Langer | 128/419 D |
| 4,504,773 | 3/1985 | Suzuki et al. | 128/419 D |
| 4,637,397 | 1/1987 | Bach, Jr. | 128/419 D |

OTHER PUBLICATIONS

Dahlback, O. et al., "Venticular Defibrillation with Square-Waves", Letters to the Editor, *The Lancet*, vol. 2, pp. 50–51, Jul. 2, 1966.

Schuder, John C. et al., "Transthoracic Ventricular Defibrillation with Square-Wave Stimuli: One-Half Cycle, One Cycle, and Multi-Cycle Waveforms", *Circulation Research*, vol. NV, pp. 258–264, Sep. 1964.

Jones, Janice L. et al., "Decreased Defilbrillator-Induced Dysfunction with Biphasic Rectangular Waveforms", Am. J. Physiology, 247 (5 Pt. 2), pp. H792–796, Nov. 1984.

*Primary Examiner*—Francis Jaworski
*Assistant Examiner*—George Manuel
*Attorney, Agent, or Firm*—Fleit, Jacobson, Cohn, Price, Holman & Stern

[57] ABSTRACT

A circuit for generating a biphasic voltage pulse to restore rhythm to a fibrillating heart, the circuit utilizing a capacitor for providing the voltage pulse. The circuit further comprises first and second thyristors to regulate the voltage and first and second electrodes to apply the regulated voltage to the fibrillating heart. The circuit further comprises an output sensing circuit that senses the exponential decay of the capacitor and signals a control circuit to switch the thyristors such that after one thyristor applies the voltage pulse to the heart in a first polarity, the other thyristor applies the voltage pulse in the opposite polarity. Therefore, substantially all energy in the capacitor is provided to the heart.

6 Claims, 2 Drawing Sheets

BIPHASIC PULSE GENERATOR FOR AN IMPLANTABLE DEFIBRILLATOR

BACKGROUND OF THE INVENTION

The present invention relates, generally, to the field of automatic implantable defibrillators. In such implantable defibrillators, the defibrillation pulse is stored and delivered by a high voltage capacitor; this capacitor is short circuited in order to terminate the defibrillation pulse.

A majority of defibrillators, found in the prior art, are short circuiting the charged capacitor which is a waste of energy. This energy could easily be applied to the fibrillating heart. Also, by short circuiting the charged capacitor, a significant amount of electrical stress is absorbed through the electronic parts of the defibrillator circuit. This electrical stress shortens the life of these parts.

One attempt to use the wasted energy of the capacitor is by using triphasic wave defibrillation. U.S. Pat. No. 4,637,397 to Jones et al discloses a defibrillator that uses a first conditioning pulse, followed by a second pulse of opposite polarity used for defibrillating, and finally a third pulse having the same polarization as the first pulse.

The following description discloses a biphasic pulse generator for an implantable defibrillator which uses only two pulses to deliver more energy stored in the charged capacitor to the fibrillating heart and thus, lowering defibrillation energy requirements.

SUMMARY OF THE INVENTION

The present invention eliminates the need to short circuit the high voltage capacitor. Thus, the stress on electronic parts is reduced. Additionally, the energy in the high voltage capacitor that was previously wasted is provided to the heart in the reverse direction, thereby reducing overall defibrillation energy requirements.

An object of the present invention is to provide a pulse generation in which a silicon controlled rectifier thyristor is turned off by means of an insulated gate transistor.

Another object of the invention is to allow a "steering" of the high voltage side of a charged capacitor to one of two electrodes while steering the low voltage side to the other electrode.

A further object of the invention is to utilize a low "on" impedance electronic switch which in the preferred embodiment is an insulated gate transistor.

Another object of the invention is to protect the limited reverse voltage handling capability of an insulated gate transistor with a diode.

A feature of the invention is that the low "on" impedance high voltage electronic switch is positioned in a low Potential gate drive circuit which obviates the use of large transformers or optical isolators in the circuit.

An advantage of the invention is that since the shorting of the high voltage capacitor has been eliminated, the stress on the electronic parts is reduced.

These, together with other objects and advantages which will become subsequently apparent, reside in the details of construction and operation as more fully hereinafter described and claimed, reference being had to the accompanying drawings forming a part hereof, wherein like numbers refer to like parts throughout.

DESCRIPTION OF THE PREFERRED EMBODIMENT

Figure 1:
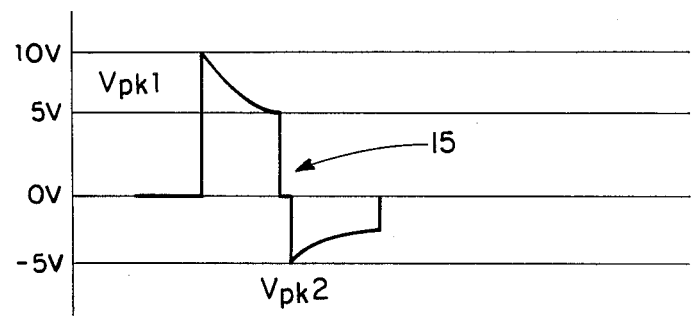
FIG. 1 shows a biphasic defibrillation pulse from a single capacitor as delivered from a circuit forming a part of the present invention.

Referring to the figures, the circuit of the present invention is designed to deliver a biphasic defibrillation pulse from a single capacitor as shown in FIG. 1. The voltage at peak 1, or Vpk1, is equal to 25 to 1000 volts delivered to the heart. After reaching Vpk1, the voltage will exponentially decay until an SCR thyristor is turned off and the high voltage side of the charged capacitor is steered to the other electrode. Now, Vpk2 is delivered to the heart in the reverse direction and is equal to 50 to 95% of Vpk1. Thus, the short circuiting of the high voltage capacitor is eliminated.

Figure 2:
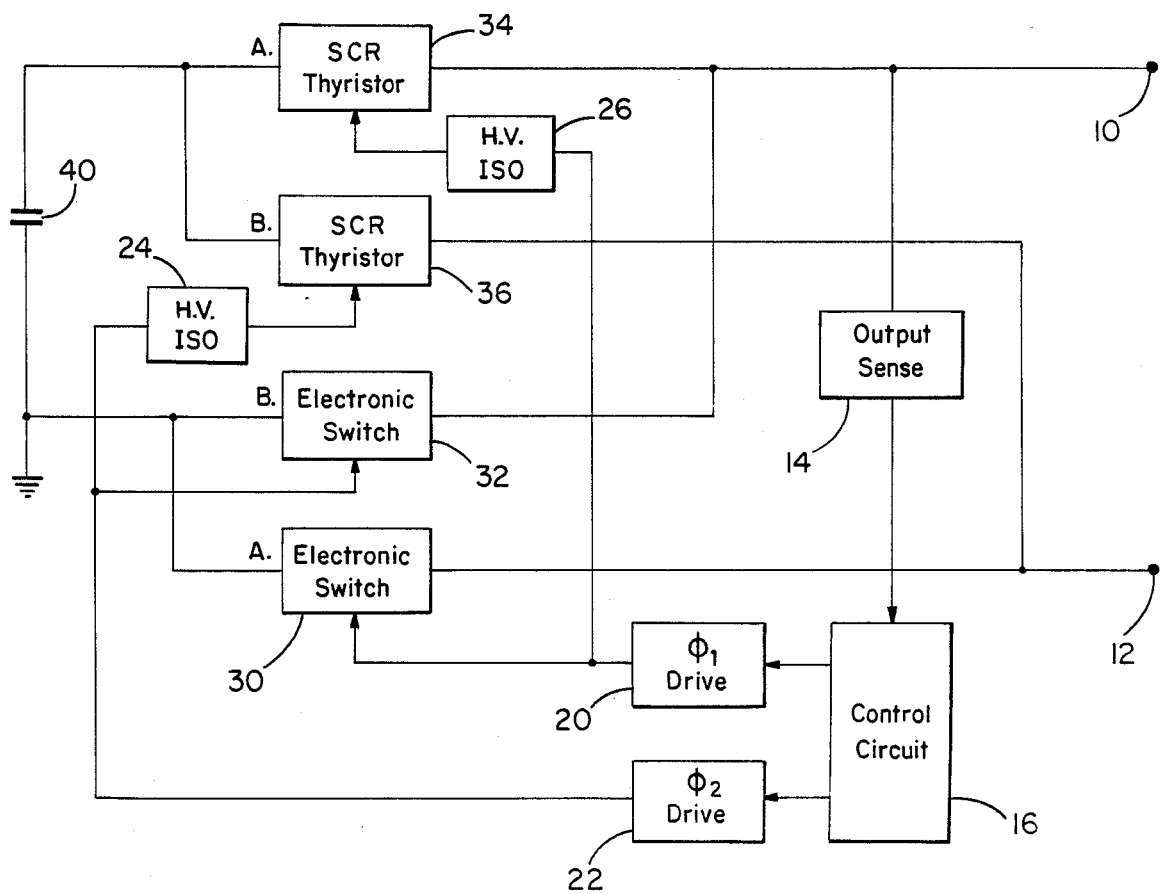
FIG. 2 shows a block diagram of the circuit of the present invention.

FIG. 2 shows the biphasic pulse generator block diagram. Control circuit 16 is a simple Four State Sequencer specifically designed to provide wait 1, phase 1, wait 2, and phase 2 states by monitoring the capacitor voltage and providing timed stimulation to the electronic switches via circuits 20 and 22. When drive circuit 20 is set high, the electronic switch 30 is allowed to conduct and thyristor 34 is turned on from drive circuit 20. At this point, the charge stored across capacitor 40 is delivered to the heart across electrodes 10 and 12 in a first polarity. After a short period of time, sensed by circuit 14, drive circuit 20 is forced low turning off electronic switch 30 and SCR 34. After a short delay, less than 500 microseconds generally indicated by numeral 15, drive circuit 22 is set high turning on electronic switch 32 and SCR 36 thus, providing an opposite current through the heart. After another period of time sensed by circuit 14, the electronic switch 32 is turned off which turns off SCR 36.

In other words, the electronic switch 30 conducts to steer the low voltage side of the main storage capacitor 40 to electrode 12 while the high side is connected to electrode 10. Electronic switch 32 conducts to steer the low voltage side of the main storage capacitor 40 to electrode 10 while the high side is connected to electrode 12.

The SCR thyristor 34, when switched "on", provides the high voltage to electrode 10. The SCR thyristor 36, when switched "on", provides the high voltage to electrode 12.

Output sense circuit 14 monitors the output to electrode 10. When the output voltage at electrode 10 falls to a suitable low level, the output sense circuit 14 will signal the control circuit 16, which then forces drive circuit 20 to a low. This shuts off electronic switch 30 and, therefore, SCR thyristor 34. When the output voltage to electrode 10 falls still further, the output sense circuit 14 signals the control circuit 16. This forces drive circuit 22 to be switched to a low, which shuts off electronic switch 32 and, therefore, the SCR thyristor 36.

The high voltage isolation transformers 24 and 26 are used to isolate the SCR system drive circuits and prevent the transmission of undesired currents to them. Also, the high voltage isolation transformers are used to separate one section of the system from undesired influences of the other sections.

Figure 3:
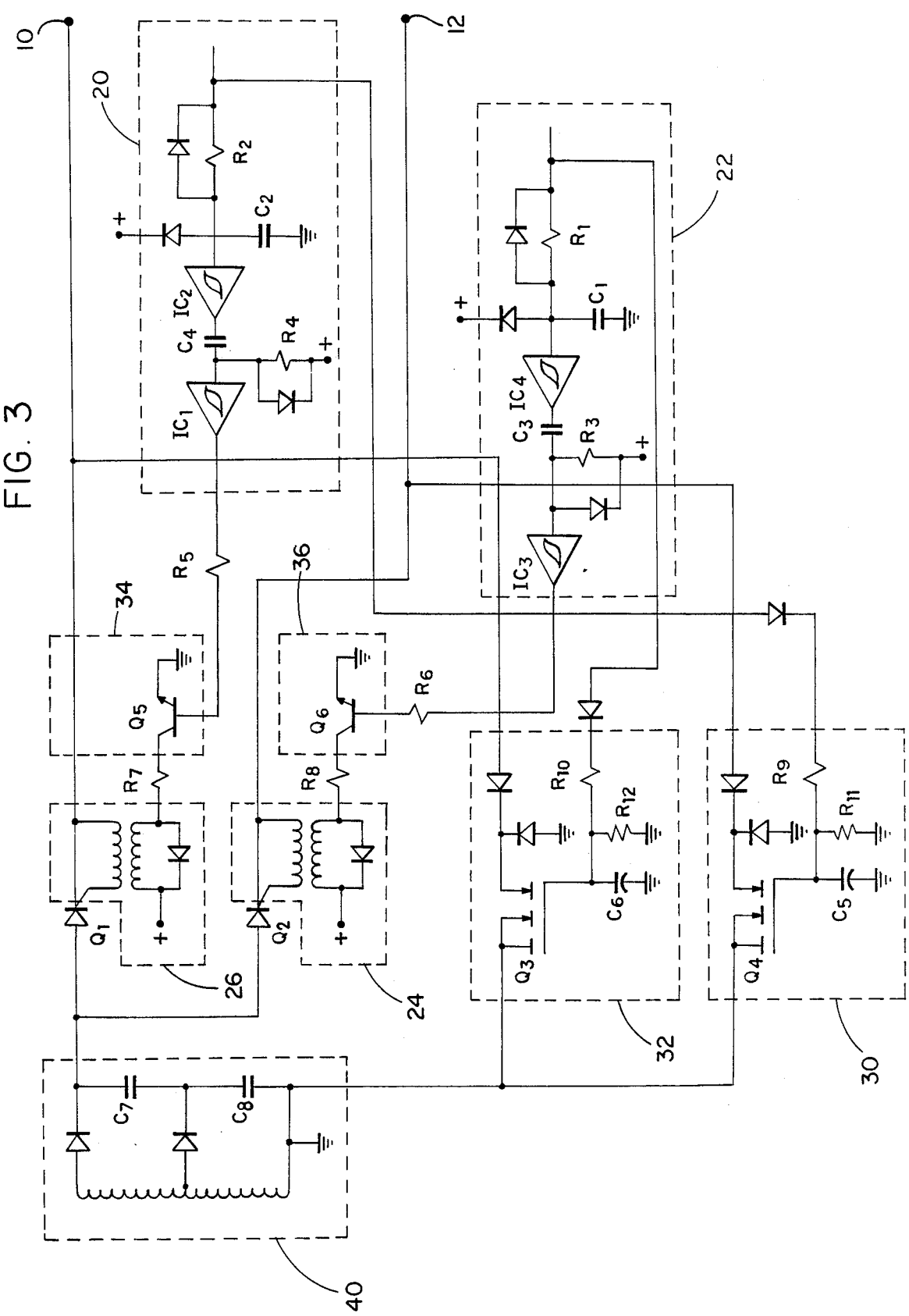
FIG. 3 shows a schematic drawing of the circuit of the present invention.

Referring to the detailed schematic shown in FIG. 3, the operation of the system is as follows. The drive circuit 20 is set high (about 10 volts) which allows the electronic switch 30 shown as an insulated gate transistor Q4 to conduct when the silicon controlled rectifier Q5, thyristor 34, is turned on from the drive circuit 20. There is a 20 microsecond delay through the network preceding the Schmidt trigger circuits IC1 and IC2 to allow switch 30 to be completely on before thyristor 34 is fired. This results in the high voltage side of the main storage capacitor 40 being switched to electrode 10 while the low side is connected to electrode 12. Now the high voltage Vpk1 is delivered to the heart.

When the output voltage falls to a suitable low level, the drive circuit 20 is set low, turning off electronic switch 30 as shown as an insulated gate transistor Q4 and, therefore, the SCR thyristor 34.

Next, after a 500 microsecond delay and drive circuit 20 has gone low, drive circuit 22 is switched to a high (i.e., approximately 10 volts). This allows electronic switch 32 shown as an insulated gate transistor Q3 to be operational and silicon controlled rectifier thyristor 36 is fired by its nominal 20 microsecond delay circuit (IC3-4 and network). The delay is again necessary to allow switch 32 to be fully on before SCR 36 is fired. The Schmidt trigger circuits IC3 and IC4 are for squaring the pulses for good logic operations. The process steers the high voltage side of capacitor 40 to electrode 12 and the low voltage side of capacitor 40 to electrode 10. Therefore, the voltage to the load is reversed and the high voltage Vpk2 is delivered to the heart.

As soon as the voltage falls to another low level, drive circuit 22 will be forced to a low and shut off electronic switch 32 shown as an insulated gate transistor Q3. Therefore, the SCR Q6 thyristor 36 will also be off.

Drive circuit 20 and drive circuit 22 are derived from a simple electronic sequence circuit which incorporates a chip such as the 14017B manufactured by Motorola. These circuits are also used to monitor the main capacitor voltage.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalencies may be resorted to, falling within the scope of the invention. One such modification is that the electronic switches 32 and 30 shown in FIG. 3 as insulated gate transistors, could also be power field effect transistors or high voltage bipolar transistors. The block diagram emphasizes the generalities by illustrating the central idea of the circuit without reference to specific circuit elements. It is, therefore, the intent that the present invention not be limited to the above but be limited only as defined in the appended claims.

What is claimed:

1. A circuit for generating a biphasic pulse to restore rhythm to a fibrillating heart, said circuit comprising:
   capacitor means for providing a voltage to restore rhythm to a fibrillating heart;
   thyristor means, connected to said capacitor means, for regulating said voltage and providing a regulated voltage;
   first electrode means, connected to said thyristor means, for receiving and applying said regulated voltage to said fibrillating heart;
   second electrode means, connected to said thyristor means, for receiving and applying said regulated voltage to said fibrillating heart;
   output sensing means, connected to said thyristor means and one of said electrode means, for sensing an exponential decay of said regulated voltage and providing a sensed signal corresponding to said sensed exponential decay; and
   control circuit means, connected to said output sensing means, for controlling said thyristor means for delivering said regulated voltage in a first polarity and subsequently in a second polarity opposite said first polarity to said fibrillating heart via said first and second electrode means.

2. A circuit for generating a biphasic pulse to restore rhythm to a fibrillating heart, said circuit comprising:
   capacitor means for providing a voltage to restore rhythm to a fibrillating heart, said capacitor means having first and second terminals;
   first and second thyristor means, both connected to said first terminal of said capacitor means, for regulating said voltage and providing a regulated voltage;
   first electrode means, connected to said first thyristor means, for receiving and applying said regulated voltage to said fibrillating heart;
   second electrode means, connected to said second thyristor means, for receiving and applying said regulated voltage to said fibrillating heart;
   output sensing means, connected to said first thyristor means and said first electrode means, for sensing an exponential decay of said regulated voltage and providing a sensed signal corresponding to said sensed exponential decay; and
   control circuit means, connected to said output sensing means, for controlling which of said first and second thyristor means is on such that when said first thyristor is on, current flows through said capacitor means for delivering said regulated voltage to the heart in a first polarity via said first and second electrode means, and when said second thyristor is on, current flows through said capacitor means for delivering said regulated voltage to the heart in a second polarity opposite said first polarity via said first and second electrode means, to restore rhythm to said fibrillating heart.

3. The circuit of claim 2, and further comprising:
   first and second drive circuits, connected to said control circuit, said first drive circuit for driving said first thyristor means and said second drive circuit for driving said second thyristor means.

4. The circuit of claim 3, and further comprising:
   a first electronic switch connected to said first drive circuit, said second electrode means, said first thyristor means, and said second terminal of said capacitor means, for forming a first circuit such that said first circuit delivers said voltage to said fibrillating heart; and
   a second electronic switch connected to said second drive circuit, said first electrode means, said second thyristor means, and said second terminal of said capacitor means, for forming a second circuit such that said second circuit delivers said voltage to said fibrillating heart.

5. The circuit of claim 2, and further comprising a capacitor discharge means for discharging said capacitor means, and wherein said capacitor means charges to a high voltage and then discharges to a low voltage.

6. The circuit of claim 2, wherein said first and second thyristor means further comprise first and second high voltage isolation transformer for isolating said first and second thyristor means.

* * * * *